United States Patent
Rosenberg (10) Patent No.: US 6,953,444 B2
(45) Date of Patent: Oct. 11, 2005

(54) INHERENT ANTI-SIPHON DEVICE

(75) Inventor: Meir Rosenberg, Newton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 410 days.

(21) Appl. No.: 10/056,285

(22) Filed: Jan. 24, 2002

(65) Prior Publication Data

US 2003/0139699 A1 Jul. 24, 2003

(51) Int. Cl.$^7$ ................................................ A61M 5/00
(52) U.S. Cl. ................................................ 604/9; 604/8
(58) Field of Search .......................... 604/8–10, 247, 604/249, 246, 256, 335, 27–28, 30, 43, 131, 523, 533, 537, 540, 93.01; 137/539, 38–3, 529–530, 510, 522, 508, 44; 128/DIG. 25; 600/29–31

(56) References Cited

U.S. PATENT DOCUMENTS

| | | | |
|---|---|---|---|
| 3,999,553 A | 12/1976 | Spitz et al. | |
| 4,413,985 A | * 11/1983 | Wellner et al. | ............... 604/9 |
| 4,551,128 A | 11/1985 | Hakim et al. | |
| 4,787,886 A | * 11/1988 | Cosman | .................... 604/9 |
| 5,176,627 A | 1/1993 | Watson | |
| 5,368,556 A | 11/1994 | Lecuyer | |
| 5,437,627 A | * 8/1995 | Lecuyer | ..................... 604/9 |
| 5,634,894 A | 6/1997 | Magram | |
| 6,090,062 A | 7/2000 | Sood et al. | |
| 6,383,160 B1 | * 5/2002 | Madsen | .................... 604/10 |

* cited by examiner

Primary Examiner—Patricia Bianco
(74) Attorney, Agent, or Firm—Nutter, McClennen & Fish, LLP (57) ABSTRACT

An anti-siphon shunt device is provided that is insensitive to body postural changes. The shunt device has a housing having a chamber, an inlet port, and an outlet port. A valve mechanism disposed within the housing manages fluid movement into and out of the chamber over a pressure gradient. The valve mechanism includes a blocking element configured to seat against an opening in a barrier mounted within the chamber for preventing fluid flow therethrough. A pressure sensor having a conformable membrane detects the external pressure surrounding the chamber and communicates with a biasing element to exert a biasing force against a first surface of the blocking element, while a second surface of the blocking element is acted upon by a countervailing pressure in a direction opposite the biasing force. The conformable membrane can be enclosed within a housing to protect the device from shutting off when a patient inadvertently lies on the valve mechanism.

23 Claims, 5 Drawing Sheets

INHERENT ANTI-SIPHON DEVICE

CROSS-REFERENCE TO RELATED APPLICATIONS

Not applicable.

STATEMENT REGARDING FEDERALLY SPONSORED RESEARCH

Not Applicable.

FIELD OF THE INVENTION

The invention relates generally to medical devices for directing bodily fluids from one region of a patient to another region. More specifically, this invention relates to shunt systems having inherent anti-siphoning properties such that the system is insensitive to postural changes in a patient.

BACKGROUND OF THE INVENTION

Shunt systems for directing body fluid from one region to another are known in the medical field. One application for such a shunt system is in the treatment of hydrocephalus, a condition where cerebrospinal fluid (CSF) collects in the ventricles of the brain of a patient. CSF is produced by the ventricular system and is normally absorbed by the venous system. However, if the CSF is not absorbed, the volume of CSF increases thereby elevating the patient's intracranial pressure. This excess CSF can result in abnormally high epidural and intradural pressures. Left untreated, hydrocephalus can result in serious medical conditions, including subdural hematoma, compression of the brain tissue, and impaired blood flow.

Figure 1:
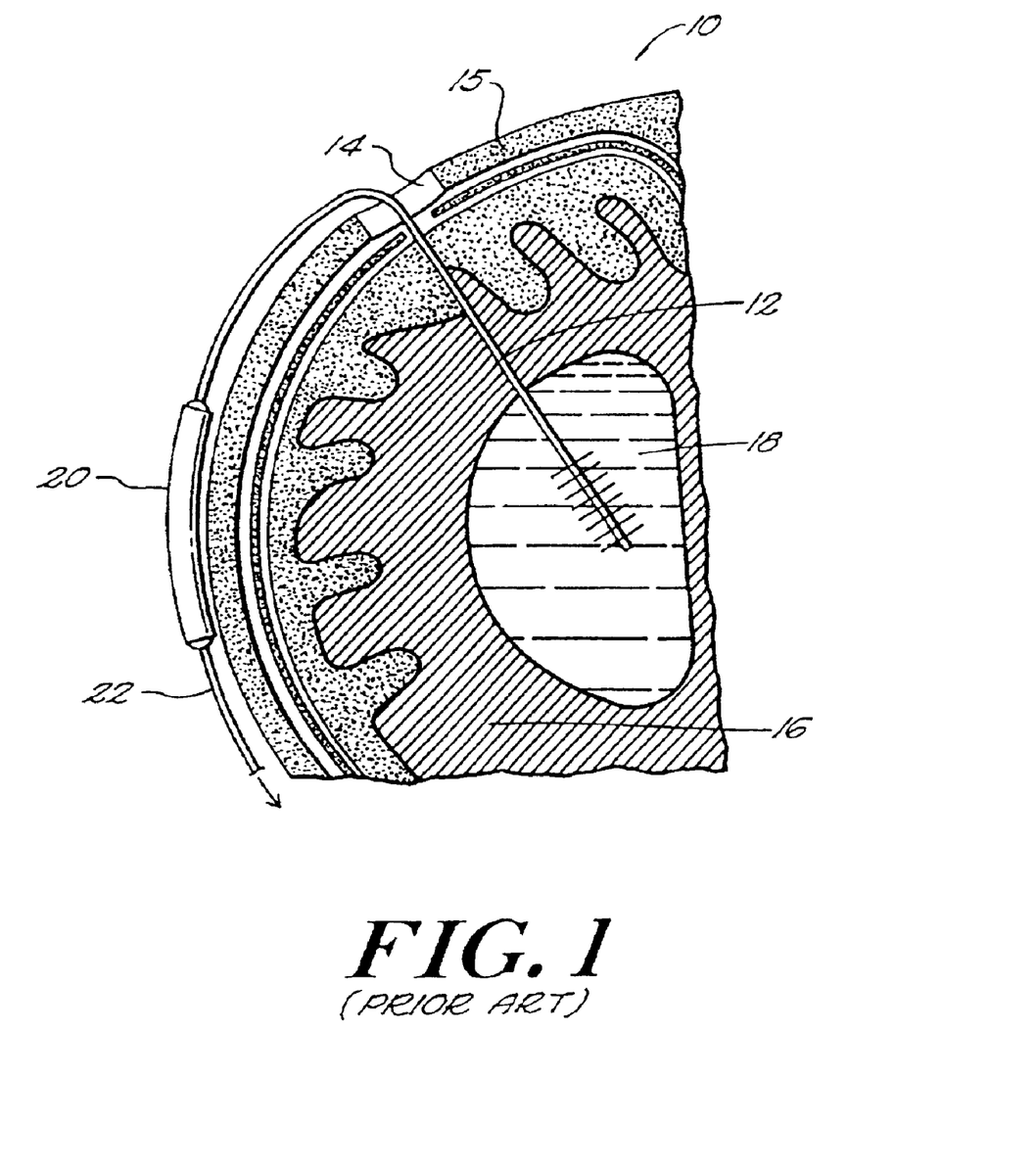
FIG. 1 is a perspective view of a prior art ventricular catheter system implanted in a patient.

Shunt systems have been developed to remove the excess CSF and to discharge the fluid to another part of the body, such as the peritoneal region. By draining the excess fluid, the elevated intracranial pressure is relieved. FIG. 1 illustrates an exemplary prior art shunt system 10 having a ventricular catheter 12 inserted through a hole 14 in the skull of a patient. The catheter 12 is advanced through brain tissue 16, and into a ventricle 18 of the brain where excess CSF is present. The catheter 12 is coupled to an inlet end of a shunt valve 20 and a drainage catheter 22 is coupled to an outlet end of the shunt valve. The shunt valve 20 is typically implanted under the scalp (not shown) of the patient. The shunt system is operative to drain excess CSF fluid from the ventricle to another part of the body, such as the right atrium, peritoneal cavity, or other locations in the body.

Generally, fluid shunt systems include a valve mechanism for controlling or regulating the flow rate of fluid through the system. Illustrative valve mechanisms operate to permit fluid flow only once the fluid pressure reaches a certain threshold level and may often permit adjustment of the pressure level at which fluid flow commences. The fluid flow rate is proportional to the pressure difference at the valve mechanism. Thus, for a pressure slightly greater than the threshold pressure level, the flow rate is relatively low. As the pressure increases the flow rate through the shunt system concomitantly increases. With these shunt systems, fluid flow normally continues until the intracranial pressure has been reduced to a level less than the threshold pressure, subject to any hysteresis of the device.

Effective fluid flow rate control is particularly important in these kinds of shunt systems since overdrainage of CSF can result in dangerous conditions, including subdural hematoma. Overdrainage tends to occur when a patient moves from a horizontal position to a sitting or standing position, due to a siphoning effect in the shunt system. That is, when the patient is lying down, the ventricle, which contains the proximal end of the shunt, is at the same elevation as the abdomen, which contains the distal end of the shunt. CSF flows out of the head normally when the pressure differential between the ventricle and the abdomen exceeds the setting of the pressure valve. However, when the patient rises to a standing or sitting position, the elevation of his head with respect to his abdomen increases. The siphoning effect is a result of the increase in the pressure differential due to gravitational effects resulting from the increased vertical height of the fluid column between the patient's head and the selected drainage location elsewhere in the patient's body. Thus, the valve may open and allow flow even though other conditions have not changed. Although such an increase in differential pressure is normal, in typical shunt systems the opening of the valve will result in undesired overdrainage, or siphoning, of the ventricular spaces.

Anti-siphon shunt systems have recently been developed which minimize the occurrence of overdrainage in patients. These anti-siphon shunt systems generally provide valve mechanisms which open, or drain, only when the intracranial pressure, or proximal pressure at the upstream side of the valve, rises above a predefined threshold pressure established in relation to some fixed reference pressure such as subcutaneous pressure. Along with the subcutaneous pressure, this predefined threshold pressure makes up the distal pressure at the downstream side of the valve. The threshold pressure can be defined by a mechanical spring preload acting upon the valve mechanism to keep it shut, which spring preload can also be adjustable and programmable by an operator. Thus, the valve mechanisms only open and allow flow when a specific proximal-distal pressure differential is achieved.

For these anti-siphoning systems to operate properly, the valve must be exposed to atmospheric pressure. This typically requires the valves to include deformable walls or apertures that are exposed to subcutaneous pressure and can translate any changes in the pressure to the valve mechanism. One of the problems with systems having deformable walls or apertures is that subcutaneous fibrotic scarring, which often develop around the shunt system once implanted, can drastically compromise the deformable wall's ability to conform and react to changes in the subcutaneous pressure. Moreover, one practical drawback with valves having deformable walls is the potential for unintentionally shutting off the valve when the patient lies on the valve and puts pressure on the deformable wall.

Accordingly, it is desirable to provide a shunt system that is effective in draining CSF in patients with hydrocephalus, while also preventing siphoning in the patient during postural changes. It is also desirable to provide such a system that is not easily compromised by subcutaneous scarring or unintentional shut off from the patient's body weight or posture. Finally, it is desirable for such a shunt system to have a low compliance biasing element acting against the valve mechanism so that the resistance of the valve to fluid flow is low.

SUMMARY OF THE INVENTION

The present invention overcomes the drawbacks inherent in prior art devices by providing an implantable anti-siphon shunt device that reduces the sensitivity of the device to a patient's postural changes. The inherent anti-siphon device of the present invention can comprise a housing having a chamber, an inlet port for passage of fluid into the chamber, and an outlet port for release of fluid out of the chamber. Disposed within the housing is a valve mechanism for managing fluid movement into and out of the chamber over a pressure gradient. The valve mechanism includes a barrier mounted within the chamber that has an opening for fluid to flow therethrough. The valve mechanism also includes a pressure sensor that detects the external pressure surrounding the chamber, and a biasing element that is in communication with the pressure sensor. Also included in the valve mechanism is a blocking element that is configured to seat against the opening of the barrier to prevent fluid to flow through the barrier. The biasing element exerts a biasing force against a first surface of the blocking element, while a second surface of the blocking element is acted upon by a countervailing pressure in a direction opposite to the biasing force.

The pressure sensor of the device can include a vent port located on the chamber. The vent port can have a conformable membrane that is susceptible to a reference pressure that is external to the chamber. The biasing element can comprise flexible bellows, while the reference pressure can be atmospheric pressure, for example. The biasing element can also be connected to the conformable membrane so that the biasing element is influenced by the reference pressure that is external to the chamber. With the device of the present invention, the displacement of the blocking element is proportional to the displacement of the biasing element.

The valve mechanism of the device of the present invention operates by managing the forces acting upon the blocking element, which is acted upon by a threshold pressure comprised of the biasing force of the biasing element and the reference pressure on the first surface, and the countervailing pressure on the second surface. The valve mechanism allows fluid to flow from one portion of the chamber through the opening in the barrier to another portion of the chamber when the countervailing pressure is greater than the threshold pressure, enabling the blocking element to be unseated from the opening. When the countervailing pressure is lower than or equal to the threshold pressure, the valve mechanism keeps the blocking element against the opening and prevents fluid flow through the barrier.

The device of the present invention is configured such that the area of the first surface of the blocking element exposed to the biasing force is substantially equal to the area of the second surface of the blocking element exposed to the countervailing pressure. In one embodiment of the present invention, the blocking element can be shaped like a spherical ball and the opening of the device can include a valve seat having a contoured surface for mating with the second surface of the blocking element to prevent fluid flow through the opening of the barrier. The biasing element can be a programmable spring mechanism or a spring mechanism having a fixed bias force. The biasing element itself can consist of a leaf spring, a coiled spring, or a helical spring.

In another embodiment of the present invention, the device comprises a housing having a chamber, an inlet port, and an outlet port. Disposed within the housing is a valve mechanism for managing fluid movement into and out of the chamber over a pressure gradient. The valve mechanism includes a barrier mounted within the chamber that has an opening for fluid to flow therethrough. The valve mechanism also includes a reference pressure chamber that detects an external pressure at a location remote from the chamber, and a biasing element that is in communication with the reference pressure chamber. Also included in the valve mechanism is a blocking element that is configured to seat against the opening of the barrier to prevent fluid to flow through the barrier. The biasing element exerts a biasing force against a first surface of the blocking element, while a second surface of the blocking element is acted upon by a countervailing pressure in a direction opposite to the biasing force. The device can have inherent anti-siphon properties.

In communication with the reference pressure chamber is an air tube connected at one end to the reference pressure chamber and to a pressure gauge at another end. The pressure gauge can comprise a flexible membrane that is susceptible to the external pressure outside of the chamber such that differences in pressure between the external pressure and the internal pressure are communicated to the conformable membrane of the reference pressure chamber. The external pressure can be, for example, the pressure within the patient's peritoneal cavity.

Further features of the invention, its nature and various advantages will be more apparent from the accompanying drawings and the following detailed description of the drawings and the preferred embodiments.

DETAILED DESCRIPTION OF THE INVENTION

Figure 2:
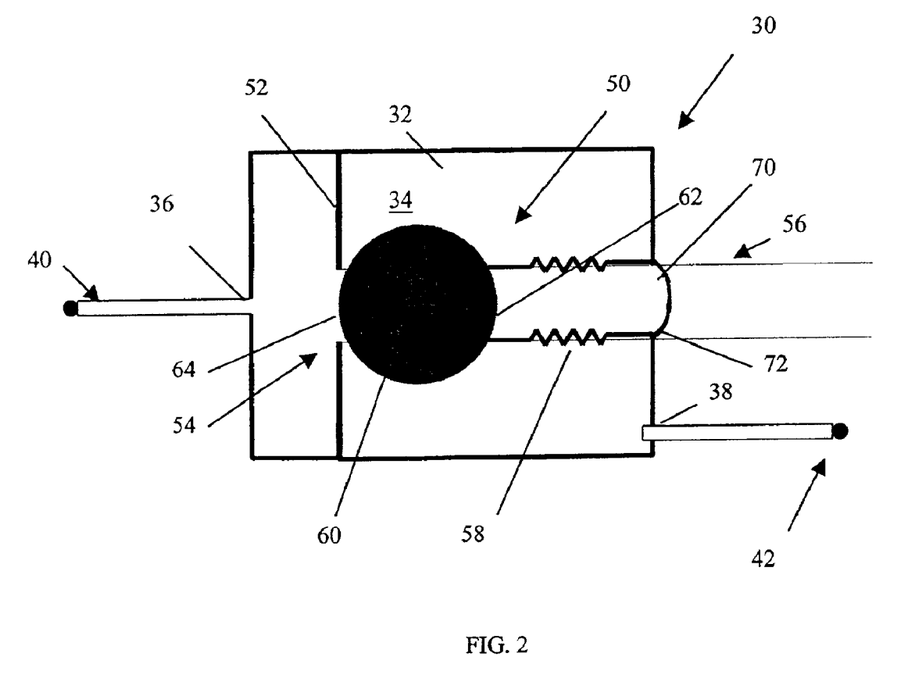
FIG. 2 is a schematic illustration of a shunt device in accordance with the present invention.

Referring now to the drawings and particularly to FIG. 2, an inherent anti-siphon shunt device 30 in accordance with the present invention is shown. The shunt device 30 can comprise a housing 32 having a chamber 34, an inlet port 36 for passage of fluid into the chamber 34, and an outlet port 38 for release of fluid out of the chamber 34. Inlet port 36 can be coupled to a ventricular catheter 40 for insertion into the ventricles of the patient's brain. Outlet port 38 can be coupled to a distal catheter 42 for draining excess cerebrospinal fluid (CSF) from the ventricles to another part of the patient's body, such as the right atrium, peritoneal cavity, or other location in the patient.

Disposed within the housing 32 is a valve mechanism 50 for managing CSF movement into and out of the chamber 34 over a pressure gradient defined by the relationship between the proximal pressure at the upstream side of the valve mechanism 50 and the distal pressure at the downstream side of the valve 50. The valve mechanism 50 includes a barrier 52 mounted within the chamber 34 that has a valve seat 54 defining an aperture for fluid to flow therethrough. The valve mechanism 50 also includes a pressure sensor 56 that detects the external pressure surrounding the chamber 34, and a biasing element 58 that is in communication with the pressure sensor 56. Also included in the valve mechanism 50 is a blocking element 60 that is configured to seat against the valve seat 54 of the barrier 52 to prevent fluid to flow through the barrier 52. The biasing element 58 exerts a biasing force against a first surface 62 of the blocking element 60, while a second surface 64 of the blocking element 60 is acted upon by a countervailing pressure in a direction opposite to the biasing force.

The pressure sensor 56 of the device 30 can include a subcutaneous vent port 70 located on the chamber 34. The subcutaneous vent port 70 can optionally include a conformable membrane 72 that is susceptible to a reference pressure external to the chamber 34 such as subcutaneous or atmospheric pressure. For example, the subcutaneous vent port 70 can comprise a fluid-filled flexible bladder. The biasing element 58 can comprise flexible bellows as shown in FIG. 2 and can also be connected to the conformable membrane 72 so that the biasing element 58 is influenced by the reference pressure external to the chamber 34. Further, biasing element 58 can be attached to blocking element 60.

The valve mechanism 50 of the device 30 operates by managing the forces acting upon the blocking element 60, which is acted upon by a threshold pressure comprised of the biasing force of the biasing element 58 and the reference pressure on the first surface 62, and the countervailing pressure on the second surface 64. In this instance, the countervailing pressure can be represented by the intracranial pressure, while the threshold pressure can be represented by the biasing force of the biasing element 58 along with the subcutaneous (atmospheric) pressure. The valve mechanism 50 allows CSF to flow from one portion of the chamber 34 through the opening 54 in the barrier 52 to another portion of the chamber 34 when the countervailing pressure is greater than the threshold pressure, enabling the blocking element 60 to be unseated from the opening 54 and opening the valve mechanism 50. When the countervailing pressure is lower than or equal to the threshold pressure, the valve mechanism 50 is closed, as a result of the threshold pressure urging the blocking element 60 against the opening 54 and preventing fluid flow through the barrier 52.

The valve mechanism 50 of the present invention is configured to have anti-siphoning properties. As shown in FIG. 2, the area of the first surface 62 of the blocking element 60 which is influenced by the threshold pressure (i.e., the portion of blocking element 60 within the biasing elements 58) is substantially equal in area to the second surface 64 of the blocking element 60 which is exposed to the countervailing pressure (see the shadowed lines representing the respective areas on the blocking element 60 that contact the valve seat 54 and the biasing elements 58). While the device works in the same manner even where the areas are slightly unequal, the nearer the areas are to being equal, the more efficient the anti-siphoning properties. Thus, by having a configuration where the areas of the blocking element 60 exposed to the threshold pressure and countervailing pressure respectively equal one another, the valve mechanism 50 of the present invention can be inherently anti-siphoning.

The mechanism by which the device 30 prevents CSF overdrainage during postural changes can best be explained with reference to FIG. 3. When a patient suddenly stands or sits upright from an inclined position, the blocking element 60 of the valve mechanism 50 is subjected to four different competing forces: the biasing force $F_b$ from the biasing element 58; the force generated by the subcutaneous pressure $F_{Sub}$; the force generated by the intracranial pressure $F_{ICP}$, i.e., the countervailing pressure; and the force generated by the downstream pressure $F_{siphon}$ due to the increased vertical height of the fluid column between the patient's head and the drainage location. In the present invention, the valve mechanism 50 is configured to open when the countervailing, or the force created by the internal pressure $F_{ICP}$ is greater than the threshold pressure comprising the forces created by the biasing force $F_b$ and the subcutaneous pressure $F_{Sub}$ to thereby unseat the blocking element 60 from its valve seat 54. This relationship can be represented by the general formula:

$$F_{ICP} > F_b + F_{Sub}$$

Figure 3:
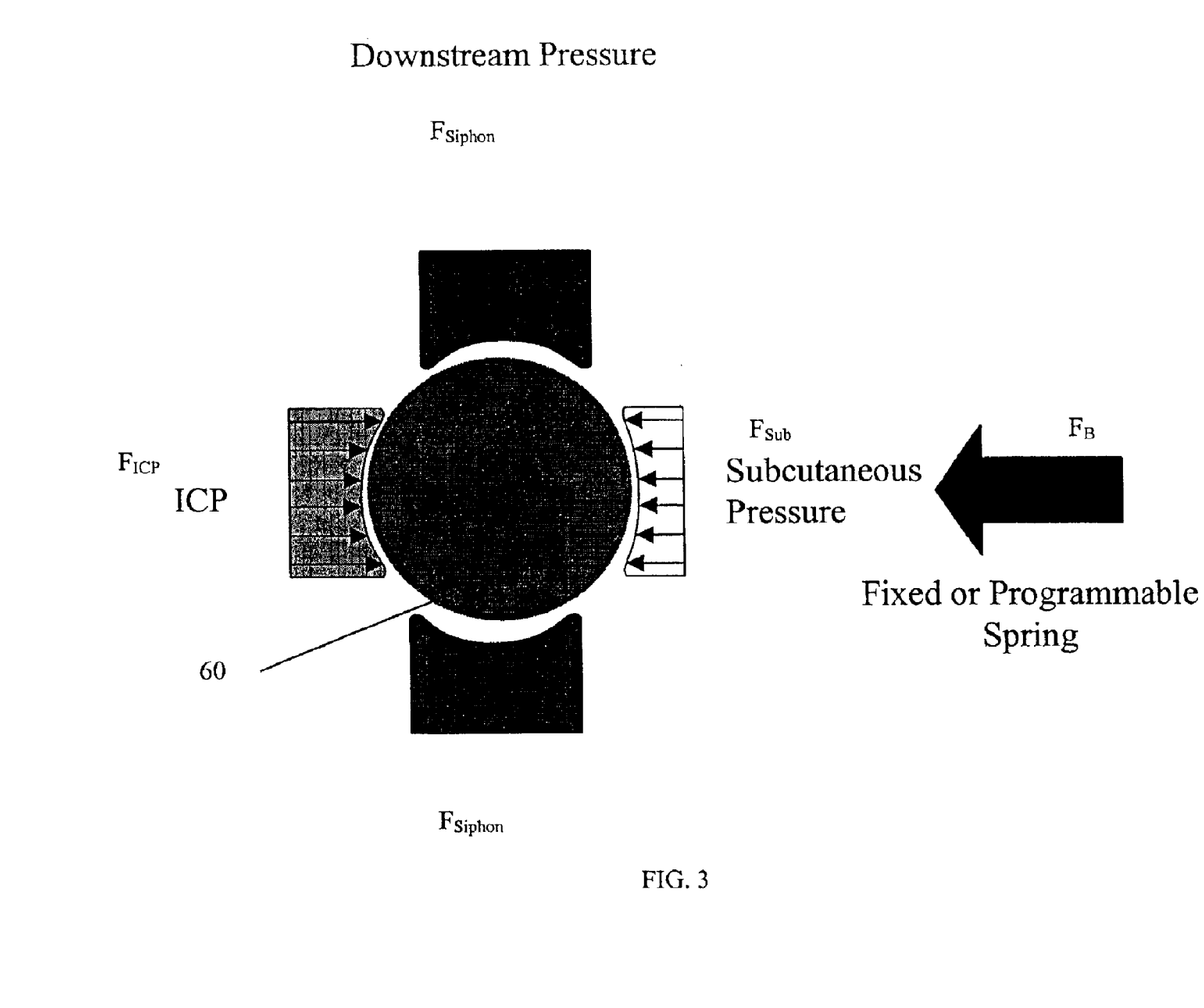
FIG. 3 is a free-body diagram of the valve mechanism of FIG. 2.

When the patient is standing or sitting upright, forces generated by downstream pressures $F_{siphon}$ act upon blocking element 60 as shown in FIG. 3. But since the valve mechanism 50 of the present invention is configured such that the forces of the downstream pressures $F_{siphon}$ are counterbalanced, i.e., the downstream pressures negate themselves because the areas exposed to the force of the siphoning pressure $F_{siphon}$ are equal on opposing faces of the blocking element 60, the opening and drainage of the shunt device 30 still follows the same general formula above. Because the areas of the blocking element 60 exposed to distal pressure are self-equilibrating, and since it is already established that the opposing faces 62, 64 of the blocking element 60 exposed to the countervailing pressure (ICP) and the threshold pressure (reference or subcutaneous pressure and biasing force), respectively, are equal in area, by negating the siphoning pressures on the valve mechanism 50 the device 30 is only responsive to pressure differences between the ventricular pressure and the threshold pressure. Hence, the opening of the valve mechanism 50 is unaffected by any postural changes in the patient, and overdrainage of CSF when the patient suddenly sits or stands is prevented.

Figure 5:
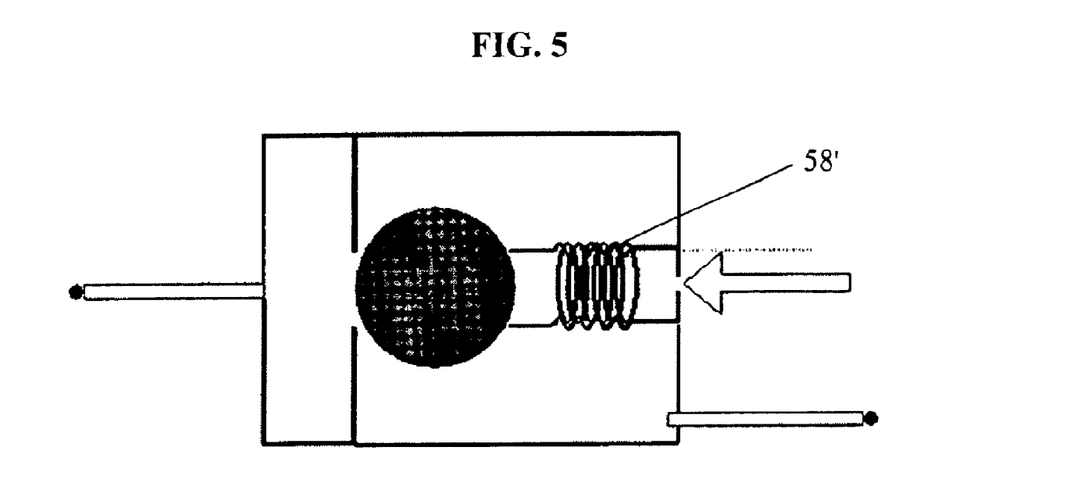
FIG. 5 is a schematic illustration of a shunt device in accordance with yet another embodiment of the present invention.

Under the general formula above, the displacement of the blocking element 60 is proportional to the displacement of the biasing element 58. Because the threshold pressure comprises the reference pressure and the biasing force from the biasing elements 58, the opening pressure of the valve mechanism 50 can be programmed by adjusting the biasing force of the biasing element 58. That is, it is possible to adjust the threshold pressure of the valve mechanism 50 by providing a programmable biasing element 58 having a spring preload controllable by the operator. As shown in FIG. 5, the biasing element 58' can be a programmable spring mechanism or a spring mechanism having a fixed bias force, as is well known to one of ordinary skill in the art, and the spring mechanism itself can consist of a leaf spring, a coiled spring, or a helical spring.

In the illustrative embodiment, the blocking element 60 can be shaped like a spherical ball and the valve seat 54 can have a contoured surface for mating with the second surface 64 of the blocking element 60 to prevent fluid flow through the opening 54 of the barrier 52. However, it is understood that the blocking element 60 can take any shape or form suitable for directing a force of predetermined magnitude in one direction, so long as its relationship with the four acting forces are consistent with the description above.

In the present invention, the biasing element 58 has a low compliance, i.e., low stiffness constant. By providing a very springy or flexible biasing element 58, the blocking element 60 can be retracted a greater distance away from the valve seat 54 and provide a larger pathway for more fluid to pass through the barrier 52 than would a very rigid or stiff biasing element. This ultimately translates into a valve mechanism 50 which has a lower resistance to fluid flow.

Suitable materials for fabricating the blocking element 60 and valve seat 54 include synthetic ruby (aluminum oxide). Suitable materials for fabricating the biasing element include stainless steel (ASTM 300 series, 316, 308, 304, and preferably 316L). The biasing element 58 is designed to bias the blocking element 60 relative to the valve seat 54 in order to provide a desired fluid flow rate through the valve seat 54. It will be appreciated by those of ordinary skill in the art that both the particular design of the biasing element 58, as well as its dimensions, e.g., thickness, and the material from which it is made, determines the relative "stiffness" of the biasing element 58 and the resulting biasing force on the blocking element 60. It is understood that flow rate can be controlled, at least in part, by altering the structure and/or design of the biasing element 58 and blocking element 60.

The shunt device 30 of the present invention is configured for implantation in a patient. As such, the components of the device 30, including the housing 32, can be fabricated with any biocompatible material for long term and/or permanent implantation within the body. Examples of such preferred materials include polymers, such as polyurethane, silicones, polyethylenes, polypropylenes, and metals such as titanium, titanium alloys, and stainless steel. Another preferable material includes polyether sulfone. Further, while it is understood that the shunt device 30 of the present invention can have any dimension deemed suitable by its operator, an exemplary length for the device 30, exclusive of any drainage catheters, is in the range of about 30 mm, while an exemplary maximum width is in the range of about 12 mm. The maximum depth of the device 30 can be in the range of about 8 mm.

Figure 4:
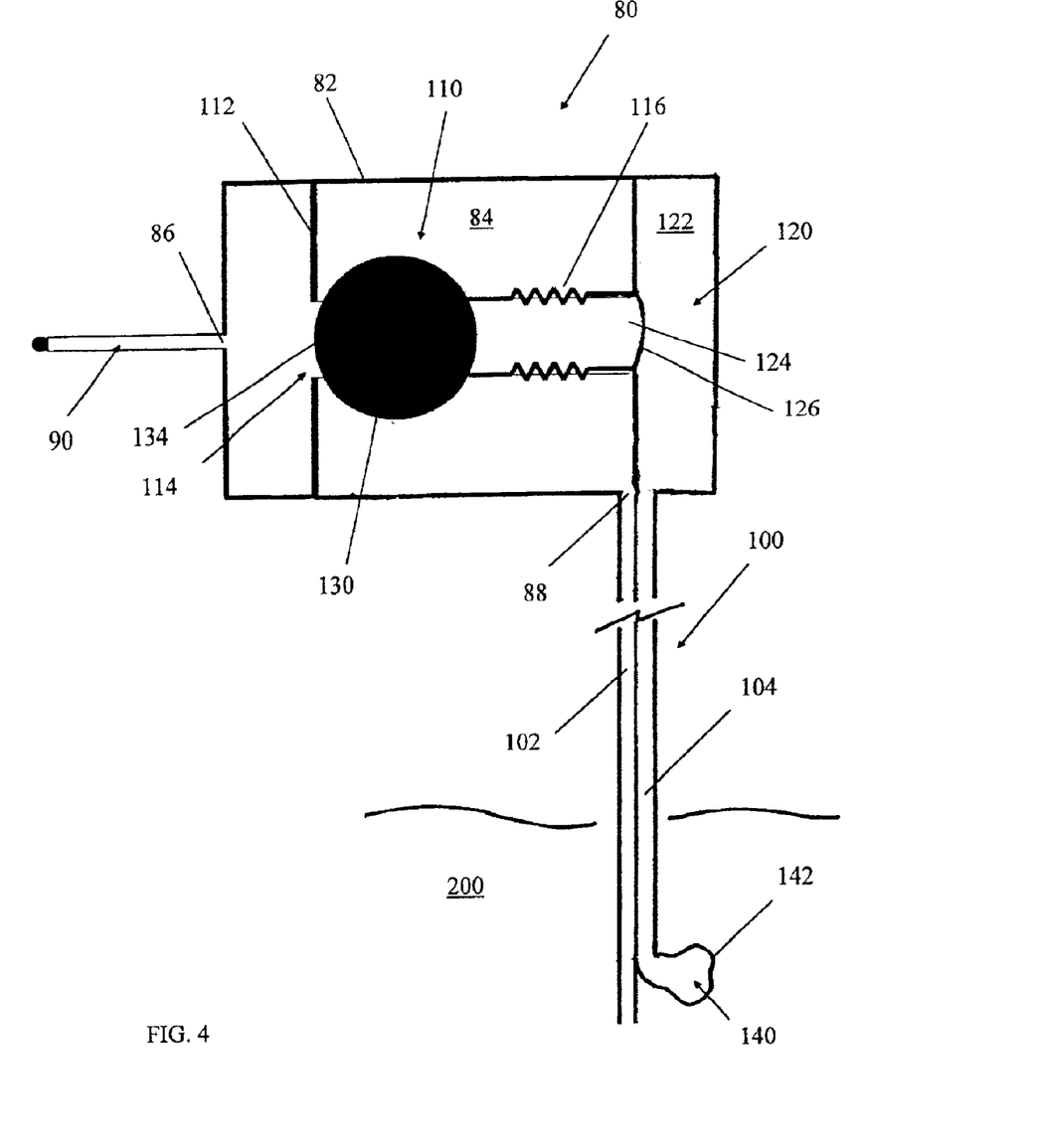
FIG. 4 is a schematic illustration of another embodiment of the shunt device in accordance with the present invention.

FIG. 4 illustrates another embodiment of the present invention, in which the shunt device 80 comprises a housing 82 having a chamber 84, an inlet port 86 for passage of fluid into the chamber 84, and an outlet port 88 for release of fluid out of the chamber 84. Inlet port 86 can be coupled to a ventricular catheter 90 for insertion into the ventricles of the patient's brain. As with device 30, a valve mechanism 110 is disposed within housing 82 for managing CSF movement into and out of the chamber 84 over a pressure gradient. The valve mechanism 110 includes a barrier 112 mounted within the chamber 84 that has a valve seat 114 defining an aperture for fluid to flow therethrough.

The valve mechanism 110 also includes a pressure sensor 120 comprising a reference pressure chamber 122 within the housing 82 that detects the external pressure surrounding the chamber 84, and a biasing element 116 that is in communication with the reference pressure chamber 122. Pressure sensor 120 can include a vent port 124 similar to device 30, which vent port 124 can optionally include a conformable membrane 126 that can be attached to biasing element 116. For example, vent port 124 can include a fluid-filled flexible bladder.

Also included in the valve mechanism 110 is a blocking element 130 that is configured to seat against the valve seat 114 of the barrier 112 to prevent fluid to flow through the barrier 112. The biasing element 116 exerts a biasing force against a first surface 132 of the blocking element 130, while a second surface 134 of the blocking element 130 is acted upon by a countervailing pressure in a direction opposite to the biasing force. Biasing element 116 can have low compliance to enable the blocking element 130 to be retracted a greater distance away from the valve seat 114 and provide a larger pathway for more fluid to pass through the barrier 112 than would a very rigid or stiff biasing element. This ultimately translates into a valve mechanism 110 which has a low resistance to fluid flow.

In communication with the reference pressure chamber 122 is an air-filled, leak-tight tube 104 connected at one end to the reference pressure chamber 122 and to a pressure gauge 140 at another end. The pressure gauge 140 can comprise a flexible membrane 142 that is susceptible to the external pressure outside of the chamber 84 such that differences in pressure between the external pressure and the internal pressure are communicated to the conformable membrane 124 of the reference pressure chamber 122. As illustrated, the external pressure can be, for example, the pressure within the patient's peritoneal cavity 200. Thus, air-filled tube 104 enables the reference pressure chamber 122 to sense the pressure in the peritoneal cavity 200. This in turn allows the valve mechanism 110 to be influenced by a threshold pressure comprising both an internal pressure, i.e., pressure within the peritoneal cavity 200, and the pressure from the biasing element 116.

The flexible membrane 142 of pressure gauge 140 can be comprised of a gas-impermeable polymer. In addition, the gas-impermeable polymer can consist of a laminate of more than one polymer. The internal surfaces of the flexible membrane 142 can also be mettalized. For example, the internal surfaces can include a metal coating or a metal layer to render the flexible membrane 142 impermeable to gases.

Preferably, the leak-tight tube 104 comprises one lumen of a double-lumen catheter 100, whereby the other lumen comprises a drainage tube 102 that is coupled at one end to outlet port 88 and wherein the opposite end extends to another region of the patient for draining excess cerebrospinal fluid (CSF) from the ventricles. In the illustrated embodiment, the fluid is drained into the peritoneal cavity 200. By providing a drainage tube 102 and leak-tight tube 104 side-by-side in this manner, the overall configuration of the device 80 is streamlined, reducing trauma to the patient during implantation and throughout its extended use.

The device 80 of the present invention provides a shunt system that is not deleteriously affected by subcutaneous fibrotic scarring, which often develop around the shunt system once implanted. In the present invention, the conformable membrane 124 of the shunt device 80 is protected by the housing 82 which shields it from damage due to growth of scar tissue around the shunt device 80. The conformable membrane 124 and the ability of the valve mechanism 110 to detect an external reference pressure is not hindered by any scar tissue formation around the shunt device 80. Having the drainage catheter 92 and the air-filled tube 140 extending into the peritoneal cavity 100 while the housing 82 encapsulates the conformable membrane 124 further protects the shunt device 80 from being unintentionally shut off such as when the patient inadvertently lies on the valve by mistake.

It is contemplated that device 80 of the present invention can optionally include anti-siphoning properties. This feature can be accomplished by providing a valve mechanism 110 where the area of the first surface 132 of the blocking element 130 which is influenced by the threshold pressure (i.e., the portion of blocking element 130 between the biasing elements 116) is equal in area to the second surface 134 of the blocking element 130 which is exposed to the countervailing pressure (see the shadowed lines representing the respective areas on the blocking element 130 that contact the valve seat 114 and the biasing elements 116), as shown in FIG. 4. By having a configuration where the areas of the blocking element 130 exposed to the threshold pressure and countervailing pressure respectively equal one another, the valve mechanism 110 of the present invention is inherently anti-siphoning.

The properties and materials of the shunt device 80 are as described above with respect to FIGS. 2 and 3. Further, while the housing configuration of shunt device 80 is described and illustrated with an anti-siphon valve mechanism 110, it is contemplated that the housing configuration where the conformable membrane is enclosed by a non-deformable chamber can be used with any type of valve mechanism for achieving the same advantages described herein. It is understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. An anti-siphon shunt device for regulating fluid flow in a patient, comprising:
    a housing defined by a chamber for fluid flow therethrough, an inlet port for passage of fluid into the chamber, and an outlet port for release of fluid from the chamber;
    a valve mechanism disposed within the housing for regulating fluid flow through the chamber over a pressure gradient, the valve mechanism including a barrier mounted within the chamber having an opening thereon for fluid flow therethrough, and a blocking element configured to seat against the opening to prevent fluid flow therethrough;
    a pressure sensor for detecting an external pressure surrounding the chamber; and
    a biasing element in communication with the pressure sensor, wherein the pressure sensor communicates with the biasing element to cause the biasing element to exert a biasing force against a first surface of the blocking element;
    wherein a countervailing pressure acts upon a second surface of the blocking element in a direction opposite to the biasing force, the area of the first surface exposed to the biasing force being substantially equal to the area of the second surface exposed to the countervailing pressure.

2. The device of claim 1, wherein the pressure sensor comprises a vent port on the chamber, the vent port including a conformable membrane susceptible to a reference pressure external to the chamber.

3. The device of claim 2, wherein the pressure sensor further comprises a reference pressure chamber enclosing the conformable membrane.

4. The device of claim 3, wherein the reference pressure chamber is in communication with an air tube, the air tube being connected at one end to the reference pressure chamber and at another end to a pressure gauge.

5. The device of claim 4, wherein the pressure gauge comprises a flexible membrane susceptible to the external pressure.

6. The device of claim 5, wherein the external pressure is within the patient's peritoneal cavity.

7. The device of claim 2, wherein the reference pressure is atmospheric pressure.

8. The device of claim 2, wherein the conformable membrane is attached to the biasing element.

9. The device of claim 1, wherein the blocking element comprises a spherical ball.

10. The device of claim 1, wherein the opening includes a valve seat having a contoured surface for mating with the second surface of the blocking element.

11. The device of claim 1, wherein the biasing element comprises flexible bellows.

12. The device of claim 1, wherein the biasing element is a programmable spring mechanism.

13. The device of claim 1, wherein the biasing element is a spring mechanism having a fixed biasing force.

14. The device of claim 1, wherein the biasing element is selected from the group consisting of a leaf spring, coiled spring, and helical spring.

15. The device of claim 1, wherein the displacement of the blocking element is proportional to the displacement of the biasing element.

16. The device of claim 1, further being configured for implantation in the patient.

17. A shunt device for regulating fluid flow in a patient, comprising:
    a housing having a chamber for fluid flow therethrough, an inlet port for passage of fluid into the chamber, and an outlet port for release of fluid from the chamber;
    a valve mechanism disposed within the housing for regulating fluid flow through the chamber over a pressure gradient; and
    a pressure sensor in communication with the valve mechanism for detecting the external pressure surrounding the chamber, the pressure sensor comprising a vent port on the housing, the vent port having a conformable membrane surrounded by a reference pressure chamber.

18. The device of claim 17, wherein the reference pressure chamber is in communication with an air tube, the tube being connected at one end to the reference pressure chamber and at another end to a pressure gauge.

19. The device of claim 18, wherein the pressure gauge comprises a flexible membrane susceptible to the external pressure.

20. The device of claim 19, wherein the external pressure is a pressure within the patient's peritoneal cavity.

21. The device of claim 18, wherein the flexible membrane is comprised of a gas-impermeable polymer.

22. The device of claim 21, wherein the impermeable polymer consists of a laminate of more than one polymer.

23. The device of claim 21, wherein the flexible membrane includes mettalized internal surfaces for rendering the membrane impermeable to gases.

* * * * *